United States Patent
Miller

(10) Patent No.: US 9,463,080 B2
(45) Date of Patent: Oct. 11, 2016

(54) FURNACE WITH THERMOELECTRIC ELEMENT

(75) Inventor: Stephan Miller, Traunstein (DE)

(73) Assignee: DEKEMA DENTAL-KREMIKÖFEN, Freilassing (DE)

( * ) Notice: Subject to any disclaimer, the term of this patent is extended or adjusted under 35 U.S.C. 154(b) by 619 days.

(21) Appl. No.: 13/642,014

(22) PCT Filed: Apr. 19, 2011

(86) PCT No.: PCT/EP2011/001994
§ 371 (c)(1),
(2), (4) Date: Oct. 18, 2012

(87) PCT Pub. No.: WO2011/131350
PCT Pub. Date: Oct. 27, 2011

(65) Prior Publication Data
US 2013/0032586 A1    Feb. 7, 2013

(30) Foreign Application Priority Data
Apr. 21, 2010    (DE) .................... 20 2010 005 938 U

(51) Int. Cl.
| A21B 1/00 | (2006.01) |
| A61C 13/20 | (2006.01) |
| F27B 17/02 | (2006.01) |
| F27D 17/00 | (2006.01) |
| F27D 99/00 | (2010.01) |
| H01L 35/30 | (2006.01) |

(52) U.S. Cl.
CPC ............ *A61C 13/20* (2013.01); *F27B 17/025* (2013.01); *F27D 17/004* (2013.01); *F27D 99/0033* (2013.01); *H01L 35/30* (2013.01)

(58) Field of Classification Search
CPC ...... A61C 13/20; F27B 17/025; F27B 21/02; F27B 21/04; F27D 17/004; F27D 99/0033; F27D 2099/006; H01L 35/30
USPC ....... 219/391, 399, 412, 482, 490, 491, 497; 373/135
See application file for complete search history.

(56) References Cited

U.S. PATENT DOCUMENTS

| 3,367,803 A * | 2/1968 | Loch ................... C04B 35/457 136/236.1 |
| 5,397,874 A * | 3/1995 | Griffith ......................... 219/497 |
| 6,019,098 A | 2/2000 | Bass et al. |

(Continued)

FOREIGN PATENT DOCUMENTS

EP    1 650 519 A1    4/2006

OTHER PUBLICATIONS

International Search Report (in German with English Translation) for PCT/EP2011/001994, mailed Jul. 27, 2011; ISA/EP.
International Preliminary Report on Patentability (in English) for PCT/EP2011/001994, issued Oct. 23, 2012; IPEA/EP.

*Primary Examiner* — Dana Ross
*Assistant Examiner* — Joseph Iskra

(57) ABSTRACT

The invention relates to a firing furnace for a tooth replacement or tooth prosthesis, with a firing chamber, at least one heating element for heating the firing chamber, a control unit for controlling the operation of the firing furnace, and a housing at least partially surrounding the firing chamber, wherein the firing furnace comprises at least one thermoelectric element for utilizing the waste heat generated by the firing furnace.

22 Claims, 1 Drawing Sheet

(56) References Cited

U.S. PATENT DOCUMENTS

2006/0088077 A1    4/2006   Jussel et al.
2006/0172245 A1    8/2006   Hu et al.
2008/0236561 A1*   10/2008   Kaiser ........................ 126/116 C
2008/0245352 A1*   10/2008   Solecki ..................... F24B 1/02
                                                                                                    126/58

\* cited by examiner

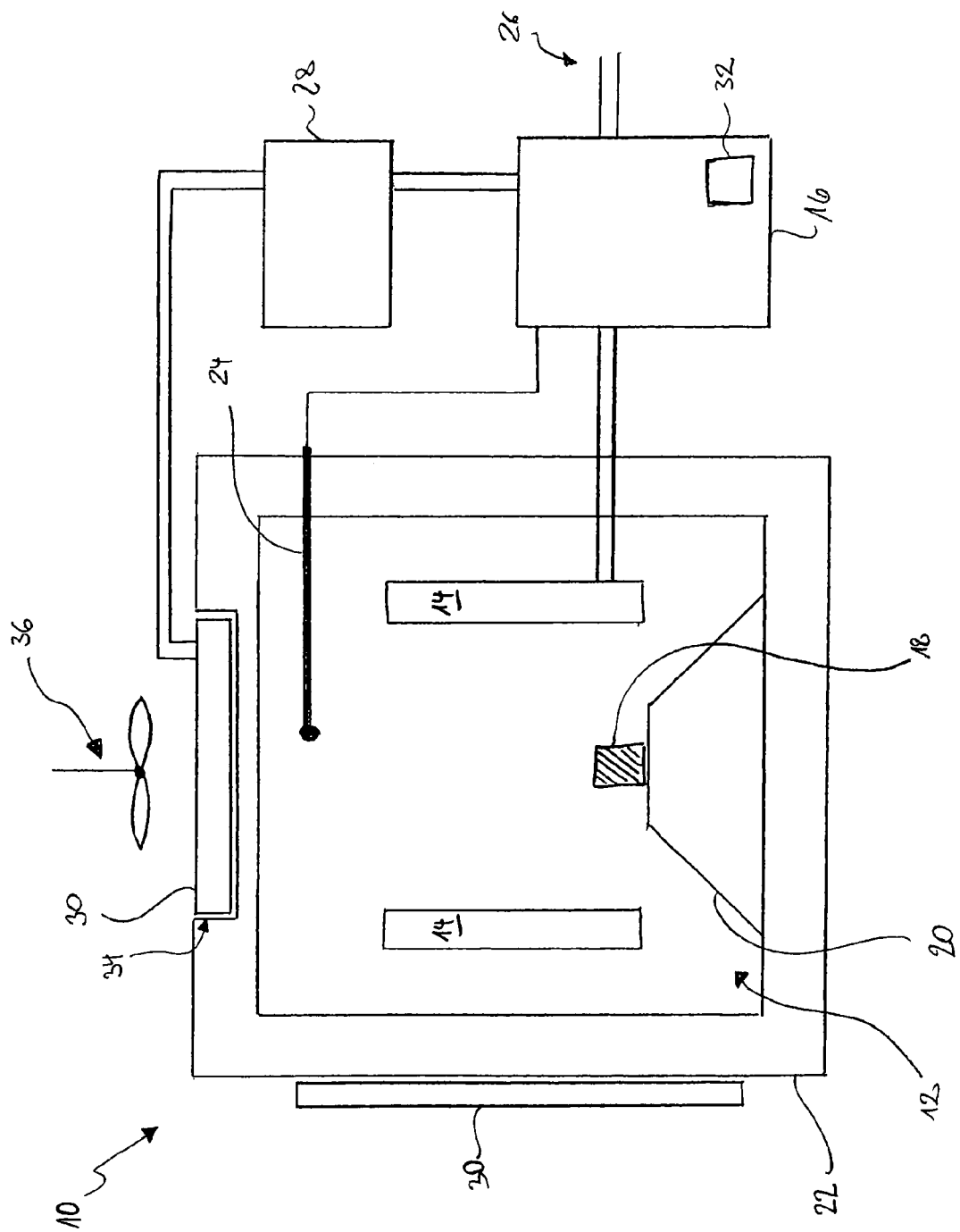

FURNACE WITH THERMOELECTRIC ELEMENT

CROSS-REFERENCE TO RELATED APPLICATIONS

This application is a 371 U.S. National Stage of International Application No. PCT/EP2011/001994, filed on Apr. 19, 2011. This application claims priority to German Application No. 20 2010 005 938.0, filed on Apr. 21, 2010. The contents of the above applications are herein incorporated by reference in their entirety.

The present invention relates to a furnace for dental prostheses or partial dental prostheses having a firing chamber, at least one heating element for heating the firing chamber, a control unit for controlling the operation of the furnace and a housing at least partly surrounding the firing chamber.

The capability for generating high temperatures, in particular in accordance with predefined temperature profiles, and the precise maintenance of the firing temperature over the required firing duration are inter alia important in furnaces of the named kind to ensure a high quality of the dental prostheses or partial dental prostheses to be fired. In addition to the above-named demands, modern furnaces should additionally work as efficiently as possible to keep the operating costs low. Such furnaces are essentially used in all regions of the world and must therefore also always be reliably functional under difficult conditions.

Usually, the energy required for the operation of the furnace is acquired from an electricity grid which is, however, subject to large fluctuations in many cases—especially in emerging market countries or developing market countries. Without any additional protective measures, a failure of the electricity grid results in a failure of the control unit, which has the consequence that, on the one hand, the heating elements are not supplied with power and, on the other hand, it is no longer possible to monitor how the temperature in the interior of the firing chamber is developing. When the electricity grid returns to normal, this normally has the result that the control unit is again set into operation and continues the firing process via the then again monitored temperature in the interior of the firing chamber. It is not clear in this situation how long the firing process was interrupted and how the temperature in the interior of the firing chamber developed during the interruption of the power supply. There is therefore no control over whether the firing material to be fired was actually exposed to conditions which still allow a continuation of the firing process without losses in quality being expected in the end product. The operator only has the choice in this situation—if the interruption of the electricity grid was noticed at all—always to treat the firing material as reject material or to classify it as a finished end product despite quality concerns.

A solution to the above-sketched problem is a provision of a conventional uninterruptible power supply (UPS). However, such UPS units are very expensive and therefore do not represent a workable alternative in many cases.

It is the underlying object of the invention to provide a furnace of the named kind which allows a reliable manufacture of dental prostheses or partial dental prostheses in an efficient manner.

This object is satisfied by a furnace having the features of claim 1.

In accordance with the invention, the furnace has at least one thermoelectric element for utilizing the waste heat generated by the furnace. In other words, the waste heat of the furnace previously emitted unused is converted by at least one thermoelectric element into electric energy which can subsequently be further used.

Suitable thermoelectric elements are, for example, based on the Seebeck effect according to which an electric voltage is formed between two points of an electric conductor which are exposed to different temperatures. With respect to the furnace, the temperature difference required for utilizing the Seebeck effect can be provided by the temperature difference between the environment of the furnace and the furnace.

Suitable thermoelectric elements are robust, can be produced in different sizes and geometries and are comparatively inexpensive. In addition, sufficiently large temperature differences can be found in the region of furnaces of the named kind so that an efficient utilization of the thermoelectric effect is possible.

Further embodiments of the invention are set forth in the dependent claims, in the description and in the drawing.

In accordance with an advantageous embodiment, the energy generated by the thermoelectric element on operation of the furnace can be supplied to the control unit and/or the heating element. This means that the energy requirements of the named functional units can be ensured wholly or at least partly by the waste heat of the oven.

An energy store can be provided which can be electrically connected to the thermoelectric element and to the control unit and/or to the heating element. This allows a buffering/intermediate storing of the energy generated by the thermoelectric element.

It is in particular advantageous in regions in which an external energy supply of the furnace (for example, by an electricity grid) has instabilities when the control, unit has a control section which is configured to establish a connection between the energy store and the control unit and/or the heating element on a failure of the external energy supply. The control section can thereby ensure the functionality of at least some important functions of the control unit and so ensure the operating security of the furnace. For example, on a failure of the external energy supply, an "emergency program" can be started which switches the furnace in a controlled manner into a safe operating mode and/or outputs suitable alarm/warning messages. The connection can in particular be established automatically so that an intervention of a user is not absolutely necessary.

Alternatively or additionally, the control unit can have a control section which is configured to establish a direct connection between the thermoelectric element and the control unit and/or the heating element on reaching a threshold value of at least one of the operating parameters of the furnace, with the connection in particular being able to be established automatically. The threshold value can be selected, for example, so that the named direct connection is automatically established when the furnace exceeds a specific temperature so that the thermoelectric element delivers sufficient energy for the operation of the control unit—or specific functions of the control unit. The direct connection can also be established in dependence on a charge state of the energy store. It is also possible to provide combinations of different operating parameters which each have to reach specific threshold values before the direct connection is established.

Differing form the above-sketched embodiments, it is also conceivable that the control unit is in permanent connection with the energy store and/or the heating element to ensure at least a limited operation on a failure of an external energy supply of the furnace without a switching over between different "energy supply modes" being required. The energy supply of the control unit thus always takes place via the energy store which is in turn connected to an external energy source.

The control unit can have a control section which is configured to monitor the state of the furnace on a failure of an external power supply of the furnace while making use of the energy generated by the thermoelectric element and can restart a complete operation of the furnace in a controlled manner on the reestablishing of the external energy supply. A complete operation is not necessarily to be understood as an operation identical to that before the supply failure. It should rather be expressed that—in contrast to a limited operation of the furnace—a full functionality of the furnace due to a sufficient energy supply is generally secured in a complete operation.

For example, in countries with highly varying grid voltages and/or comparatively frequent grid outages, a kind of "emergency program" can be carried out by the control section which monitors and/or records the state of the oven, in particular the temperature development in the interior of the oven, during an insufficient supply of the furnace with external energy. The carrying out of the emergency program can advantageously be automatically set in motion by the control section.

The acquired monitoring data can be utilized to decide whether the running firing process has to be aborted or whether it can be continued after reestablishment of the external energy supply—possibly with modified parameters (firing duration, temperature profile, . . . )—without the dental prostheses or partial dental prostheses to be fired suffering quality losses. It is understood that the control section can also output warning messages of the most varied kind to indicate the failure of the external energy supply to the operator and to allow the initiation of corresponding counter-measures.

The thermoelectric element is preferably arranged at the housing or integrated in the housing. A thermal insulation of the housing can be carried out with less insulation, can in particular be cut away, in the region of the thermoelectric element relative to other regions of the housing to generate a thermal gradient between the housing and the environment which is suitable for an effective thermoelectric energy generation in operation of the furnace. The housing in particular has a cut-out in which the thermoelectric element is at least partly arranged.

To generate a suitable thermal gradient, a cooling device can be provided with which at least one side of the thermoelectric element remote from the firing chamber can be cooled.

It must be pointed out that generally any desired number of thermoelectric elements can be provided at or in the housing to utilize the waste heat generated by the furnace in an advantageous manner. For example, a plurality of sides, or even all the sides, of the housing can be provided with thermoelectric elements over a large area to be able to use the waste heat as efficiently as possible. However, only individual sides of the housing can also be partly or completely provided with thermoelectric elements if, for example, an uninterruptible operation of the control unit only has to be ensured for a relatively short time period and grid fluctuations are only to be expected very rarely.

An advantageous embodiment of the invention will be explained in the following purely by way of example with reference to the enclosed drawing.

The FIGURE shows a furnace 10 with a firing chamber 12 which is heatable by heating elements 14. The heating elements 14 are connected to a control unit 16 which controls their operation to generate a suitable temperature profile (temperature-time profile) during a firing process in the interior of the firing chamber. For reasons of clarity, only the connection of the right hand heating element 14 to the control unit 16 is shown. The temperature in the interior of the firing chamber 12 is monitored by a temperature sensor 24 which is likewise connected to the control unit 16.

A firing material 18 to be fired in the furnace 10 is arranged on a firing tray 20 in the interior of the firing chamber 12. The firing chamber 12 is surrounded by a housing 22 which has a thermally insulating effect. The housing 22 must be able to cope with large temperature differences since temperatures of approximately 1600° C. can easily be reached during the firing process in the interior of the firing chamber 12, whereas the outside of the housing 22 should as a rule not considerably exceed the environmental temperature in order, for example, not to represent any risk for the operator.

The furnace 10 acquires the energy required for its operation from an external electricity grid 26. To ensure a reliable operation of the furnace 10 also with instabilities of the electricity grid 26, it includes an energy store 28 which is connected to thermoelectric elements 30 (only the connection of the upper thermoelectric element 30 to the energy store 28 is shown for reasons of clarity). The thermoelectric elements 30 utilize the waste heat of the furnace 10 for power generation and feed the generated power into the energy store 28 which keeps the control unit 16 at least partly functional as required—for example, on an outage of the electricity grid 26.

The control unit 16 includes a monitoring section 32 which recognizes the failure of the electricity grid 26, for example in that a falling below of a threshold value of the grid voltage is recognized, and automatically establishes a connection of the energy store 28 to the control unit 16 to continue to operate at least the temperature sensor 24 and to store the determined temperature data in a data store. Depending on the dimensions of the energy store 28, a maintenance of the operation of the heating elements 14—optionally in part—can also be provided, for example in order not to fall below critical temperature thresholds in the interior of the firing chamber 12. The control unit 16 can thus at least maintain an "emergency operation" and can record the state of the furnace 10 and in particular the temperature in the interior of the firing chamber 12 so that a check can be made whether the firing material 18 is to be treated as reject goods or not.

Alternatively to the embodiment shown, the energy store 28 can also be permanently connected to the control unit 16. It is also possible that the supply with external energy takes place via the energy store 28.

The supply of the control unit 16 with sufficient energy during the failure of the grid voltage 26 also allows the restarting of the firing process after the restoration of the power supply, with use being able to be made of the recorded state data for an optimum restart of the firing process. For this purpose, corresponding parameter records can be stored in the control unit 16. The parameter records contain a respective series of operating parameters for problem cases/interruption scenarios, which are realistically to be expected, which allow a controlled start-up of the furnace 10 and a continuation of the firing process adapted to the respective present situation. I.e. individual parameters or a plurality of parameters of the firing process are modified on the basis of the recorded measured values and the stored parameter records to obtain a flawless firing material 18 despite this interruption.

The thermoelectric elements 30 can, differing from the embodiment shown, surround the housing 22 substantially at all sides to utilize the waste heat of the furnace 10 even more efficiently. The housing 22 can advantageously be designed so that a temperature occurs at its outer side which is sufficiently high to heat the thermoelectric elements 30 sufficiently highly at its side facing the housing 22. The other side of the thermoelectric elements 30 faces a colder temperature level (environmental temperature) so that the Seebeck effect generating a voltage can be formed.

It is particularly efficient to provide at least one cut-out 34 in the housing in which one of the thermoelectric elements 30 is arranged. This thermoelectric element 30 is thereby integrated into the housing 22—at least in part. The thermal insulation function of the housing 22 is reduced in the region of the cut-out 34 so that the temperature gradient required for the operation of the thermoelectric element 30 can be provided in locally restricted form and is at least partly replaced with the insulation effect of the thermoelectric element 30.

For example, a temperature of a maximum of approximately 300° C. is present at the side of the thermoelectric elements 30 facing the firing chamber 12, whereas the side of the thermoelectric elements 30 remote from the firing chamber 12 has an environmental temperature of approximately 30° C.

There are thermoelectric elements which reach a performance of more than 10 watts at a temperature difference of 270° C., which in many cases is easily sufficient for the operation of relevant functional regions of a typical control unit. It is furthermore possible to use thermoelectric elements in the furnace 10 which also act as an energy store in addition to their actual thermoelectric effect.

To support the formation of a temperature difference between the two sides of the thermoelectric elements 30, a cooling device 36 can be provided which is shown by way of example in the enclosed drawing by a stylized fan. It is, however, also possible—additionally or alternatively—to provide cooling ribs and/or a liquid cooling.

The invention claimed is:

1. A furnace for dental prostheses or partial dental prostheses, the furnace comprising:
   a firing chamber;
   at least one heating element for heating the firing chamber;
   a control unit for controlling the operation of the furnace;
   a housing at least partly surrounding the firing chamber, the housing including a first portion having a first thickness and a second portion adjacent to the first portion and having a second thickness that is greater than the first thickness; and
   a thermoelectric element for utilizing the waste heat generated by the furnace, wherein:
   the thermoelectric element is disposed outside of the firing chamber and directly adjacent to an outer surface of the housing;
   the thermoelectric element has a third thickness; and
   a sum of the third thickness of the thermoelectric element and the first thickness of the first portion of the housing is less than or equal to the second thickness of the second portion of the housing.

2. A furnace in accordance with claim 1, wherein the thermoelectric element is integrated into the housing, is disposed entirely outside of the firing chamber, and has at least one side that is exposed to ambient air.

3. A furnace in accordance with claim 1, wherein the energy generated by the thermoelectric element in operation of the furnace is supplied to at least one of the control unit and the heating element.

4. A furnace in accordance with claim 1, wherein an energy store is provided and is electrically connected to the thermoelectric element and to the control unit and/or to the heating element.

5. A furnace in accordance with claim 4, wherein the control unit has a control section which is configured to establish a connection between the energy store and the control unit and/or the heating element on a failure of an external energy supply.

6. A furnace in accordance with claim 5, wherein the connection is established automatically.

7. A furnace in accordance with claim 1, wherein the control unit has a control section which is configured to establish a direct connection between the thermoelectric element and the control unit and/or the heating element on the reaching of a threshold value of an operating parameter of the furnace.

8. A furnace in accordance with claim 7, wherein the connection is established automatically.

9. A furnace in accordance with claim 4, wherein the control unit and/or the heating element are permanently connected to the energy store.

10. A furnace in accordance with claim 1, wherein the control unit has a control section which is configured to monitor the state of the furnace in a restricted state of operation on a failure of an external power supply of the furnace while making use of the energy generated by the thermoelectric element and to restart a complete operation of the furnace in a controlled manner on the restoring of the external power supply.

11. A furnace in accordance with claim 1, wherein the thermoelectric element is arranged at the housing.

12. A furnace in accordance with claim 11, wherein a thermal insulation of the housing in the region of the thermoelectric element is made less insulating relative to other regions of the housing.

13. A furnace in accordance with claim 12, wherein the thermal insulation is cut away in the region of the thermoelectric element.

14. A furnace in accordance with claim 11, wherein the housing has a cut-out in which the thermoelectric element is at least partly arranged.

15. A furnace in accordance with claim 1, wherein a cooling device is provided with which at least one side of the thermoelectric element remote from the firing chamber can be cooled.

16. A furnace in accordance with claim 1, wherein the thermoelectric element is disposed entirely outside of the firing chamber and has at least one side that is exposed to ambient air.

17. A furnace in accordance with claim 1, wherein the thermoelectric element is disposed directly adjacent to the outer surface of the first portion of the housing.

18. A furnace in accordance with claim 1 wherein:
   the outer surface of the housing defines a pocket; and
   the thermoelectric element is disposed in the pocket.

19. A furnace in accordance with claim 18, wherein the thermoelectric element is disposed entirely within the pocket.

20. A furnace in accordance with claim 1, wherein the thermoelectric element has a first side that faces the housing and a second side opposite the first side that is exposed to ambient air.

21. A furnace in accordance with claim 18, wherein the outer surface of the first portion of the housing is recessed relative to the outer surface of the second portion of the housing to form the pocket.

22. A furnace in accordance with claim 21, wherein the outer surface of the first portion of the housing is recessed relative to the outer surface of the second portion of the housing by an amount that is equal to a difference between the first thickness of the first portion and the second thickness of the second portion.

* * * * *

UNITED STATES PATENT AND TRADEMARK OFFICE
CERTIFICATE OF CORRECTION

PATENT NO. : 9,463,080 B2  
APPLICATION NO. : 13/642014  
DATED : October 11, 2016  
INVENTOR(S) : Miller Page 1 of 7

It is certified that error appears in the above-identified patent and that said Letters Patent is hereby corrected as shown below:

Please delete Patent 9,463,080 B2 in its entirety and insert Patent 9,463,080 B2 in its entirety as shown on the attached pages.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*

(12) United States Patent
Miller

(10) Patent No.: US 9,463,080 B2
(45) Date of Patent: Oct. 11, 2016

(54) FURNACE WITH THERMOELECTRIC ELEMENT

(75) Inventor: Stephan Miller, Traunstein (DE)

(73) Assignee: DEKEMA DENTAL-KERAMIKÖFEN, Freilassing (DE)

(*) Notice: Subject to any disclaimer, the term of this patent is extended or adjusted under 35 U.S.C. 154(b) by 619 days.

(21) Appl. No.: 13/642,014

(22) PCT Filed: Apr. 19, 2011

(86) PCT No.: PCT/EP2011/001994
§ 371 (c)(1),
(2), (4) Date: Oct. 18, 2012

(87) PCT Pub. No.: WO2011/131350
PCT Pub. Date: Oct. 27, 2011

(65) Prior Publication Data
US 2013/0032586 A1    Feb. 7, 2013

(30) Foreign Application Priority Data
Apr. 21, 2010   (DE) .................. 20 2010 005 938 U

(51) Int. Cl.
*A21B 1/00*   (2006.01)
*A61C 13/20*  (2006.01)
*F27B 17/02*  (2006.01)
*F27D 17/00*  (2006.01)
*F27D 99/00*  (2010.01)
*H01L 35/30*  (2006.01)

(52) U.S. Cl.
CPC .......... *A61C 13/20* (2013.01); *F27B 17/025* (2013.01); *F27D 17/004* (2013.01); *F27D 99/0033* (2013.01); *H01L 35/30* (2013.01)

(58) Field of Classification Search
CPC ........ A61C 13/20; F27B 17/025; F27B 21/02; F27B 21/04; F27D 17/004; F27D 99/0033; F27D 2099/006; H01L 35/30
USPC ....... 219/391, 399, 412, 482, 490, 491, 497; 373/135
See application file for complete search history.

(56) References Cited

U.S. PATENT DOCUMENTS

| 3,367,803 | A | * | 2/1968 | Loch ................... C04B 35/457 |
|---|---|---|---|---|
| | | | | 136/236.1 |
| 5,397,874 | A | * | 3/1995 | Griffith ....................... 219/497 |
| 6,019,098 | A | | 2/2000 | Bass et al. |
| 2006/0088077 | A1 | | 4/2006 | Jussel et al. |
| 2006/0172245 | A1 | | 8/2006 | Hu et al. |
| 2008/0236561 | A1 | * | 10/2008 | Kaiser ....................... 126/116 C |
| 2008/0245352 | A1 | * | 10/2008 | Solecki ..................... F24B 1/02 |
| | | | | 126/58 |

FOREIGN PATENT DOCUMENTS

EP      1 650 519 A1    4/2006

OTHER PUBLICATIONS

International Search Report (in German with English Translation) for PCT/EP2011/001994, mailed Jul. 27, 2011; ISA/EP.
International Preliminary Report on Patentability (in English) for PCT/EP2011/001994, issued Oct. 23, 2012; IPEA/EP.

* cited by examiner

*Primary Examiner* — Dana Ross
*Assistant Examiner* — Joseph Iskra

(57) ABSTRACT

The invention relates to a firing furnace for a tooth replacement or tooth prosthesis, with a firing chamber, at least one heating element for heating the firing chamber, a control unit for controlling the operation of the firing furnace, and a housing at least partially surrounding the firing chamber, wherein the firing furnace comprises at least one thermoelectric element for utilizing the waste heat generated by the firing furnace.

22 Claims, 1 Drawing Sheet

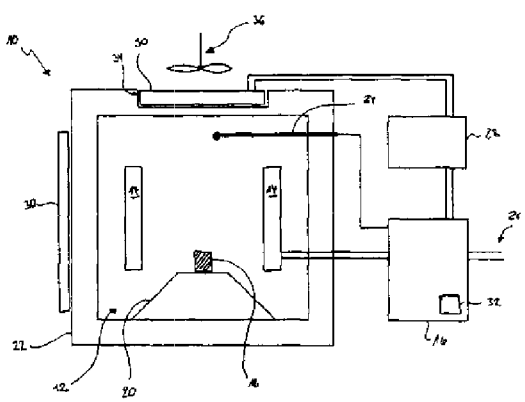

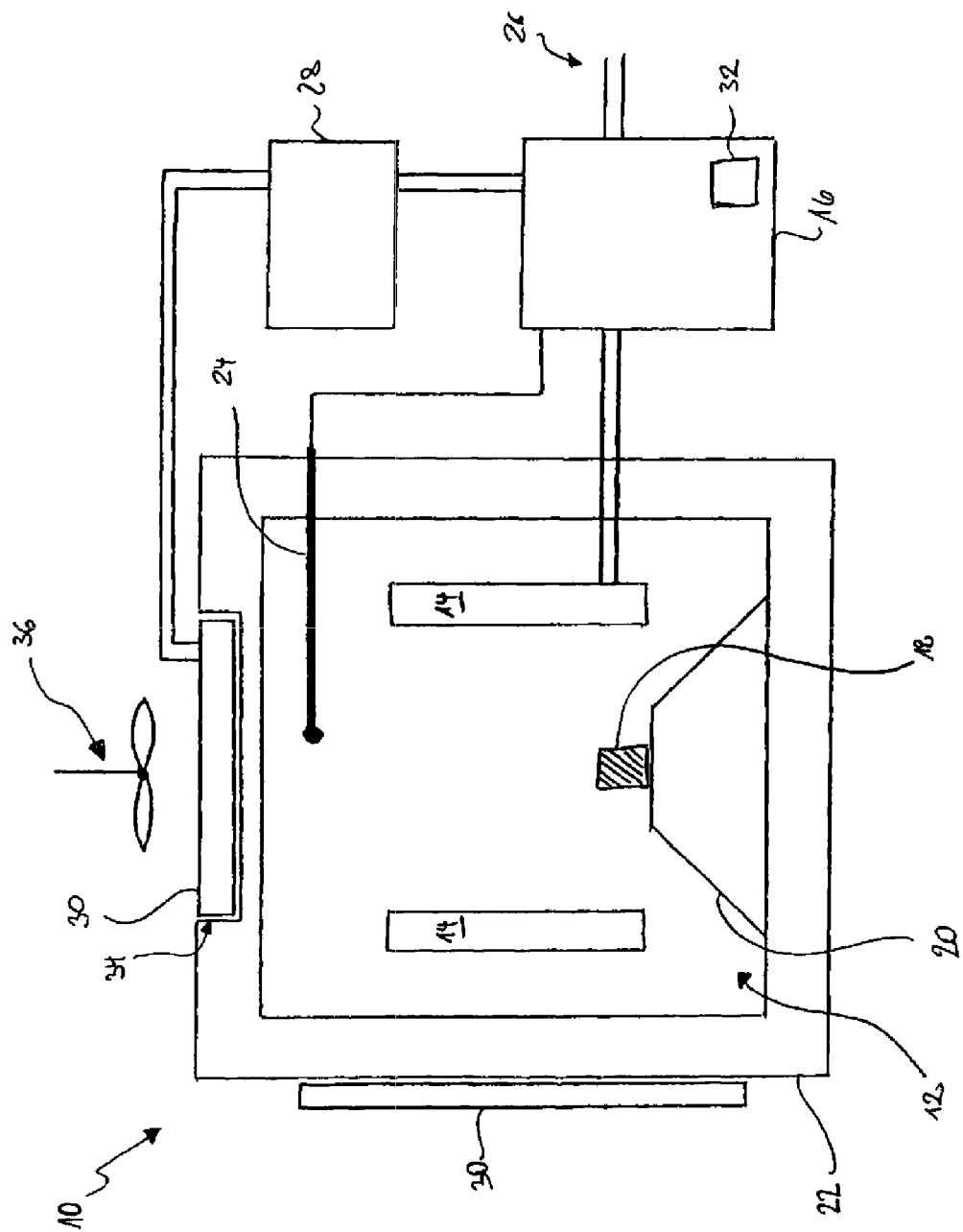

FURNACE WITH THERMOELECTRIC ELEMENT

CROSS-REFERENCE TO RELATED APPLICATIONS

This application is a 371 U.S. National Stage of International Application No. PCT/EP2011/001994, filed on Apr. 19, 2011. This application claims priority to German Application No. 20 2010 005 938.0, filed on Apr. 21, 2010. The contents of the above applications are herein incorporated by reference in their entirety.

The present invention relates to a furnace for dental prostheses or partial dental prostheses having a firing chamber, at least one heating element for heating the firing chamber, a control unit for controlling the operation of the furnace and a housing at least partly surrounding the firing chamber.

The capability for generating high temperatures, in particular in accordance with predefined temperature profiles, and the precise maintenance of the firing temperature over the required firing duration are inter alia important in furnaces of the named kind to ensure a high quality of the dental prostheses or partial dental prostheses to be fired. In addition to the above-named demands, modern furnaces should additionally work as efficiently as possible to keep the operating costs low. Such furnaces are essentially used in all regions of the world and must therefore also always be reliably functional under difficult conditions.

Usually, the energy required for the operation of the furnace is acquired from an electricity grid which is, however, subject to large fluctuations in many cases—especially in emerging market countries or developing market countries. Without any additional protective measures, a failure of the electricity grid results in a failure of the control unit, which has the consequence that, on the one hand, the heating elements are not supplied with power and, on the other hand, it is no longer possible to monitor how the temperature in the interior of the firing chamber is developing. When the electricity grid returns to normal, this normally has the result that the control unit is again set into operation and continues the firing process via the then again monitored temperature in the interior of the firing chamber. It is not clear in this situation how long the firing process was interrupted and how the temperature in the interior of the firing chamber developed during the interruption of the power supply. There is therefore no control over whether the firing material to be fired was actually exposed to conditions which still allow a continuation of the firing process without losses in quality being expected in the end product. The operator only has the choice in this situation—if the interruption of the electricity grid was noticed at all—always to treat the firing material as reject material or to classify it as a finished end product despite quality concerns.

A solution to the above-sketched problem is a provision of a conventional uninterruptible power supply (UPS). However, such UPS units are very expensive and therefore do not represent a workable alternative in many cases.

It is the underlying object of the invention to provide a furnace of the named kind which allows a reliable manufacture of dental prostheses or partial dental prostheses in an efficient manner.

This object is satisfied by a furnace having the features of claim 1.

In accordance with the invention, the furnace has at least one thermoelectric element for utilizing the waste heat generated by the furnace. In other words, the waste heat of the furnace previously emitted unused is converted by at least one thermoelectric element into electric energy which can subsequently be further used.

Suitable thermoelectric elements are, for example, based on the Seebeck effect according to which an electric voltage is formed between two points of an electric conductor which are exposed to different temperatures. With respect to the furnace, the temperature difference required for utilizing the Seebeck effect can be provided by the temperature difference between the environment of the furnace and the furnace.

Suitable thermoelectric elements are robust, can be produced in different sizes and geometries and are comparatively inexpensive. In addition, sufficiently large temperature differences can be found in the region of furnaces of the named kind so that an efficient utilization of the thermoelectric effect is possible.

Further embodiments of the invention are set forth in the dependent claims, in the description and in the drawing.

In accordance with an advantageous embodiment, the energy generated by the thermoelectric element on operation of the furnace can be supplied to the control unit and/or the heating element. This means that the energy requirements of the named functional units can be ensured wholly or at least partly by the waste heat of the oven.

An energy store can be provided which can be electrically connected to the thermoelectric element and to the control unit and/or to the heating element. This allows a buffering/intermediate storing of the energy generated by the thermoelectric element.

It is in particular advantageous in regions in which an external energy supply of the furnace (for example, by an electricity grid) has instabilities when the control, unit has a control section which is configured to establish a connection between the energy store and the control unit and/or the heating element on a failure of the external energy supply. The control section can thereby ensure the functionality of at least some important functions of the control unit and so ensure the operating security of the furnace. For example, on a failure of the external energy supply, an "emergency program" can be started which switches the furnace in a controlled manner into a safe operating mode and/or outputs suitable alarm/warning messages. The connection can in particular be established automatically so that an intervention of a user is not absolutely necessary.

Alternatively or additionally, the control unit can have a control section which is configured to establish a direct connection between the thermoelectric element and the control unit and/or the heating element on reaching a threshold value of at least one of the operating parameters of the furnace, with the connection in particular being able to be established automatically. The threshold value can be selected, for example, so that the named direct connection is automatically established when the furnace exceeds a specific temperature so that the thermoelectric element delivers sufficient energy for the operation of the control unit—or specific functions of the control unit. The direct connection can also be established in dependence on a charge state of the energy store. It is also possible to provide combinations of different operating parameters which each have to reach specific threshold values before the direct connection is established.

Differing form the above-sketched embodiments, it is also conceivable that the control unit is in permanent connection with the energy store and/or the heating element to ensure at least a limited operation on a failure of an external energy supply of the furnace without a switching over between different "energy supply modes" being required. The energy supply of the control unit thus always takes place via the energy store which is in turn connected to an external energy source.

The control unit can have a control section which is configured to monitor the state of the furnace on a failure of an external power supply of the furnace while making use of the energy generated by the thermoelectric element and can restart a complete operation of the furnace in a controlled manner on the reestablishing of the external energy supply. A complete operation is not necessarily to be understood as an operation identical to that before the supply failure. It should rather be expressed that—in contrast to a limited operation of the furnace—a full functionality of the furnace due to a sufficient energy supply is generally secured in a complete operation.

For example, in countries with highly varying grid voltages and/or comparatively frequent grid outages, a kind of "emergency program" can be carried out by the control section which monitors and/or records the state of the oven, in particular the temperature development in the interior of the oven, during an insufficient supply of the furnace with external energy. The carrying out of the emergency program can advantageously be automatically set in motion by the control section.

The acquired monitoring data can be utilized to decide whether the running firing process has to be aborted or whether it can be continued after reestablishment of the external energy supply—possibly with modified parameters (firing duration, temperature profile, . . . )—without the dental prostheses or partial dental prostheses to be fired suffering quality losses. It is understood that the control section can also output warning messages of the most varied kind to indicate the failure of the external energy supply to the operator and to allow the initiation of corresponding counter-measures.

The thermoelectric element is preferably arranged at the housing or integrated in the housing. A thermal insulation of the housing can be carried out with less insulation, can in particular be cut away, in the region of the thermoelectric element relative to other regions of the housing to generate a thermal gradient between the housing and the environment which is suitable for an effective thermoelectric energy generation in operation of the furnace. The housing in particular has a cut-out in which the thermoelectric element is at least partly arranged.

To generate a suitable thermal gradient, a cooling device can be provided with which at least one side of the thermoelectric element remote from the firing chamber can be cooled.

It must be pointed out that generally any desired number of thermoelectric elements can be provided at or in the housing to utilize the waste heat generated by the furnace in an advantageous manner. For example, a plurality of sides, or even all the sides, of the housing can be provided with thermoelectric elements over a large area to be able to use the waste heat as efficiently as possible. However, only individual sides of the housing can also be partly or completely provided with thermoelectric elements if, for example, an uninterruptible operation of the control unit only has to be ensured for a relatively short time period and grid fluctuations are only to be expected very rarely.

An advantageous embodiment of the invention will be explained in the following purely by way of example with reference to the enclosed drawing.

The FIGURE shows a furnace 10 with a firing chamber 12 which is heatable by heating elements 14. The heating elements 14 are connected to a control unit 16 which controls their operation to generate a suitable temperature profile (temperature-time profile) during a firing process in the interior of the firing chamber. For reasons of clarity, only the connection of the right hand heating element 14 to the control unit 16 is shown. The temperature in the interior of the firing chamber 12 is monitored by a temperature sensor 24 which is likewise connected to the control unit 16.

A firing material 18 to be fired in the furnace 10 is arranged on a firing tray 20 in the interior of the firing chamber 12. The firing chamber 12 is surrounded by a housing 22 which has a thermally insulating effect. The housing 22 must be able to cope with large temperature differences since temperatures of approximately 1600° C. can easily be reached during the firing process in the interior of the firing chamber 12, whereas the outside of the housing 22 should as a rule not considerably exceed the environmental temperature in order, for example, not to represent any risk for the operator.

The furnace 10 acquires the energy required for its operation from an external electricity grid 26. To ensure a reliable operation of the furnace 10 also with instabilities of the electricity grid 26, it includes an energy store 28 which is connected to thermoelectric elements 30 (only the connection of the upper thermoelectric element 30 to the energy store 28 is shown for reasons of clarity). The thermoelectric elements 30 utilize the waste heat of the furnace 10 for power generation and feed the generated power into the energy store 28 which keeps the control unit 16 at least partly functional as required—for example, on an outage of the electricity grid 26.

The control unit 16 includes a monitoring section 32 which recognizes the failure of the electricity grid 26, for example in that a falling below of a threshold value of the grid voltage is recognized, and automatically establishes a connection of the energy store 28 to the control unit 16 to continue to operate at least the temperature sensor 24 and to store the determined temperature data in a data store. Depending on the dimensions of the energy store 28, a maintenance of the operation of the heating elements 14—optionally in part—can also be provided, for example in order not to fall below critical temperature thresholds in the interior of the firing chamber 12. The control unit 16 can thus at least maintain an "emergency operation" and can record the state of the furnace 10 and in particular the temperature in the interior of the firing chamber 12 so that a check can be made whether the firing material 18 is to be treated as reject goods or not.

Alternatively to the embodiment shown, the energy store 28 can also be permanently connected to the control unit 16. It is also possible that the supply with external energy takes place via the energy store 28.

The supply of the control unit 16 with sufficient energy during the failure of the grid voltage 26 also allows the restarting of the firing process after the restoration of the power supply, with use being able to be made of the recorded state data for an optimum restart of the firing process. For this purpose, corresponding parameter records can be stored in the control unit 16. The parameter records contain a respective series of operating parameters for problem cases/interruption scenarios, which are realistically to be expected, which allow a controlled start-up of the furnace 10 and a continuation of the firing process adapted to the respective present situation. I.e. individual parameters or a plurality of parameters of the firing process are modified on the basis of the recorded measured values and the stored parameter records to obtain a flawless firing material 18 despite this interruption.

The thermoelectric elements 30 can, differing from the embodiment shown, surround the housing 22 substantially at all sides to utilize the waste heat of the furnace 10 even more efficiently. The housing 22 can advantageously be designed so that a temperature occurs at its outer side which is sufficiently high to heat the thermoelectric elements 30 sufficiently highly at its side facing the housing 22. The other side of the thermoelectric elements 30 faces a colder temperature level (environmental temperature) so that the Seebeck effect generating a voltage can be formed.

It is particularly efficient to provide at least one cut-out 34 in the housing in which one of the thermoelectric elements 30 is arranged. This thermoelectric element 30 is thereby integrated into the housing 22—at least in part. The thermal insulation function of the housing 22 is reduced in the region of the cut-out 34 so that the temperature gradient required for the operation of the thermoelectric element 30 can be provided in locally restricted form and is at least partly replaced with the insulation effect of the thermoelectric element 30.

For example, a temperature of a maximum of approximately 300° C. is present at the side of the thermoelectric elements 30 facing the firing chamber 12, whereas the side of the thermoelectric elements 30 remote from the firing chamber 12 has an environmental temperature of approximately 30° C.

There are thermoelectric elements which reach a performance of more than 10 watts at a temperature difference of 270° C., which in many cases is easily sufficient for the operation of relevant functional regions of a typical control unit. It is furthermore possible to use thermoelectric elements in the furnace 10 which also act as an energy store in addition to their actual thermoelectric effect.

To support the formation of a temperature difference between the two sides of the thermoelectric elements 30, a cooling device 36 can be provided which is shown by way of example in the enclosed drawing by a stylized fan. It is, however, also possible—additionally or alternatively—to provide cooling ribs and/or a liquid cooling.

The invention claimed is:

1. A furnace for dental prostheses or partial dental prostheses, the furnace comprising:
a firing chamber;
at least one heating element for heating the firing chamber;
a control unit for controlling the operation of the furnace;
a housing at least partly surrounding the firing chamber, the housing including a first portion having a first thickness and a second portion adjacent to the first portion and having a second thickness that is greater than the first thickness; and
a thermoelectric element for utilizing the waste heat generated by the furnace, wherein:
the thermoelectric element is disposed outside of the firing chamber and directly adjacent to an outer surface of the housing;
the thermoelectric element has a third thickness; and
a sum of the third thickness of the thermoelectric element and the first thickness of the first portion of the housing is less than or equal to the second thickness of the second portion of the housing.

2. A furnace in accordance with claim 1, wherein the thermoelectric element is integrated into the housing, is disposed entirely outside of the firing chamber, and has at least one side that is exposed to ambient air.

3. A furnace in accordance with claim 1, wherein the energy generated by the thermoelectric element in operation of the furnace is supplied to at least one of the control unit and the heating element.

4. A furnace in accordance with claim 1, wherein an energy store is provided and is electrically connected to the thermoelectric element and to the control unit and/or to the heating element.

5. A furnace in accordance with claim 4, wherein the control unit has a control section which is configured to establish a connection between the energy store and the control unit and/or the heating element on a failure of an external energy supply.

6. A furnace in accordance with claim 5, wherein the connection is established automatically.

7. A furnace in accordance with claim 1, wherein the control unit has a control section which is configured to establish a direct connection between the thermoelectric element and the control unit and/or the heating element on the reaching of a threshold value of an operating parameter of the furnace.

8. A furnace in accordance with claim 7, wherein the connection is established automatically.

9. A furnace in accordance with claim 4, wherein the control unit and/or the heating element are permanently connected to the energy store.

10. A furnace in accordance with claim 1, wherein the control unit has a control section which is configured to monitor the state of the furnace in a restricted state of operation on a failure of an external power supply of the furnace while making use of the energy generated by the thermoelectric element and to restart a complete operation of the furnace in a controlled manner on the restoring of the external power supply.

11. A furnace in accordance with claim 1, wherein the thermoelectric element is arranged at the housing.

12. A furnace in accordance with claim 11, wherein a thermal insulation of the housing in the region of the thermoelectric element is made less insulating relative to other regions of the housing.

13. A furnace in accordance with claim 12, wherein the thermal insulation is cut away in the region of the thermoelectric element.

14. A furnace in accordance with claim 11, wherein the housing has a cut-out in which the thermoelectric element is at least partly arranged.

15. A furnace in accordance with claim 1, wherein a cooling device is provided with which at least one side of the thermoelectric element remote from the firing chamber can be cooled.

16. A furnace in accordance with claim 1, wherein the thermoelectric element is disposed entirely outside of the firing chamber and has at least one side that is exposed to ambient air.

17. A furnace in accordance with claim 1, wherein the thermoelectric element is disposed directly adjacent to the outer surface of the first portion of the housing.

18. A furnace in accordance with claim 1 wherein:
the outer surface of the housing defines a pocket; and
the thermoelectric element is disposed in the pocket.

19. A furnace in accordance with claim 18, wherein the thermoelectric element is disposed entirely within the pocket.

20. A furnace in accordance with claim 1, wherein the thermoelectric element has a first side that faces the housing and a second side opposite the first side that is exposed to ambient air.

21. A furnace in accordance with claim 18, wherein the outer surface of the first portion of the housing is recessed relative to the outer surface of the second portion of the housing to form the pocket.

22. A furnace in accordance with claim 21, wherein the outer surface of the first portion of the housing is recessed relative to the outer surface of the second portion of the housing by an amount that is equal to a difference between the first thickness of the first portion and the second thickness of the second portion.

* * * * *